United States Patent
Bianco et al.

(10) Patent No.: US 10,632,246 B2
(45) Date of Patent: Apr. 28, 2020

(54) CONTAINER FOR CLOSING CAPS FOR SYRINGES

(71) Applicant: Health Robotics S.r.l., Bolzano (IT)

(72) Inventors: Walter Bianco, Trieste (IT); Gabriele Kucich, Trieste (IT); Fabio Fioravanti, Trieste (IT)

(73) Assignee: Health Robotics S.r.l., Bolzano (IT)

( * ) Notice: Subject to any disclaimer, the term of this patent is extended or adjusted under 35 U.S.C. 154(b) by 177 days.

(21) Appl. No.: 15/747,730

(22) PCT Filed: Jul. 28, 2016

(86) PCT No.: PCT/IB2016/054527
§ 371 (c)(1),
(2) Date: Jan. 25, 2018

(87) PCT Pub. No.: WO2017/017640
PCT Pub. Date: Feb. 2, 2017

(65) Prior Publication Data
US 2019/0001049 A1    Jan. 3, 2019

(30) Foreign Application Priority Data
Jul. 28, 2015    (IT) .................. 102015000038846

(51) Int. Cl.
*A61M 5/00*    (2006.01)
*A61M 5/31*    (2006.01)

(52) U.S. Cl.
CPC .......... *A61M 5/002* (2013.01); *A61M 5/3134* (2013.01); *A61M 2005/3104* (2013.01); *A61M 2207/10* (2013.01)

(58) Field of Classification Search
CPC ............... A61M 5/002; A61M 5/3134; A61M 2005/3104; A61M 2007/10
USPC ........................................................ 206/364
See application file for complete search history.

(56) References Cited

U.S. PATENT DOCUMENTS

| | | | | |
|---|---|---|---|---|
| 3,074,540 A | * | 1/1963 | Beich .................... | A61M 5/002 206/366 |
| 3,625,353 A | * | 12/1971 | Ishii ........................ | A61L 2/26 206/365 |
| 4,932,418 A | * | 6/1990 | Coburn .............. | A61B 5/15003 600/576 |
| 4,944,730 A | * | 7/1990 | Plucinski .............. | A61M 5/008 206/366 |
| 5,092,462 A | * | 3/1992 | Sagstetter ........... | A61M 5/3205 206/366 |

(Continued)

FOREIGN PATENT DOCUMENTS

| WO | WO 2002/011797 A1 | 2/2002 |
|---|---|---|
| WO | WO 2013/088178 A1 | 6/2013 |
| WO | WO 2013/122941 A1 | 8/2013 |

OTHER PUBLICATIONS

PCT International Search Report and Written Opinion for PCT/IB2016/054527 dated Nov. 9, 2016.

*Primary Examiner* — Ernesto A Grano
(74) *Attorney, Agent, or Firm* — McCarter & English, LLP

(57) ABSTRACT

A container for closing caps for syringes has a plurality of seats, each of which is suited to be engaged, in a sliding manner, by a respective closing cap, and has a movable portion configured to move between a locking position of the relevant closing cap in the seat and a release position.

12 Claims, 4 Drawing Sheets

(56) References Cited

U.S. PATENT DOCUMENTS

| | | | | |
|---|---|---|---|---|
| 5,545,145 | A * | 8/1996 | Clinton | A61M 5/002 206/366 |
| 5,829,589 | A * | 11/1998 | Nguyen | A61M 5/002 206/366 |
| 5,873,462 | A * | 2/1999 | Nguyen | A61M 5/002 206/366 |
| 5,968,021 | A * | 10/1999 | Ejlersen | A61M 5/3213 206/365 |
| 5,971,966 | A * | 10/1999 | Lav | A61M 5/002 206/365 |
| 6,059,758 | A * | 5/2000 | Padilla | A61M 5/3213 604/192 |
| 6,488,666 | B1 * | 12/2002 | Geist | A61M 5/3213 604/192 |
| 6,591,984 | B2 * | 7/2003 | Odierno | A61M 5/008 206/365 |
| 6,889,830 | B2 * | 5/2005 | Bergeron | A61M 5/3205 206/365 |
| 9,186,452 | B2 * | 11/2015 | DiBiasi | A61M 5/008 |
| 9,694,129 | B2 * | 7/2017 | Banik | A61M 5/3204 |
| 2002/0014430 | A1 * | 2/2002 | Groth | A61M 5/002 206/438 |
| 2002/0020646 | A1 * | 2/2002 | Groth | A61M 5/002 206/366 |
| 2002/0020647 | A1 * | 2/2002 | Groth | A61M 5/002 206/366 |
| 2003/0121812 | A1 * | 7/2003 | Sprieck | A61B 17/205 206/365 |
| 2004/0064095 | A1 * | 4/2004 | Vitello | A61M 5/3134 604/111 |
| 2010/0063457 | A1 * | 3/2010 | Crossman | A61M 5/002 604/263 |
| 2011/0071475 | A1 * | 3/2011 | Horvath | A61M 5/002 604/192 |
| 2011/0290799 | A1 * | 12/2011 | Anderson | A61M 5/31511 220/200 |
| 2015/0025473 | A1 * | 1/2015 | Banik | A61M 5/3204 604/192 |

* cited by examiner

CONTAINER FOR CLOSING CAPS FOR SYRINGES

CROSS-REFERENCE TO RELATED APPLICATIONS

This application is a 35 U.S.C. § 371 National Stage filing of International Application No. PCT/IB2016/054527 filed on Jul. 28, 2016, which claims priority to Italian Patent Application IT 102015000038846 filed on Jul. 28, 2015.

TECHNICAL FIELD

The present invention concerns a container for closing caps for syringes.

The present invention can be applied particularly advantageously in a screwdriver assembly for screw-fastening closing caps for syringes used in the preparation of injectable pharmaceutical products, to which the following discussion will explicitly refer without loss of generality.

BACKGROUND ART

In the sector of the preparation of injectable pharmaceutical products, the production of a machine comprising at least one magazine for a plurality of bags, syringes and bottles is well known; at least one dosing station for the preparation of a pharmaceutical product obtained by feeding into a syringe a drug taken from a bottle and a diluent taken from a bag; and a holding and transport device to transfer bags, syringes and bottles between the magazine and the dosing station.

The syringe comprises a container cylinder, a piston engaged in a sliding manner in the container cylinder, and a needle screw-fastened on one open end of the container cylinder.

Once the pharmaceutical product has been prepared inside the syringe, the needle is removed from the syringe and the open end is sealed by means of a closing cap to allow the medical personnel to handle the syringe safely.

The closing caps are screwed onto the open ends of the relevant syringes by a screwdriver assembly comprising a vibrating plate shaped to house inside it a plurality of closing caps, a pocket adapted to receive and retain the closing cap fed each time through the outlet of the vibrating plate, and a supporting device for supporting the syringes.

The pocket and the supporting device are moved with respect to each other by a roto-translatory motion so as to screw the closing cap onto the open end of the syringe.

The magazine, the dosing station, the holding and transport device, and the screwdriver assembly are housed inside a container frame provided with at least one access door.

Since the closing caps are packaged in blisters, the machines for preparing the known pharmaceutical products of the kind described above have some drawbacks mainly deriving from the fact that operations for extraction of the closing caps from the relevant blisters and loading the closing caps on the vibrating plate of the screwdriver assembly via the access door must be performed manually by the personnel in charge on the outside of the container frame and can therefore compromise the sterility of the closing caps.

DISCLOSURE OF INVENTION

The object of the present invention is to produce a container for closing caps for syringes which is free from the drawbacks described above and is simple and inexpensive to implement.

According to the present invention a container for closing caps for syringes is produced as claimed in the attached claims.

BRIEF DESCRIPTION OF THE DRAWINGS

The present invention will now be described with reference to the accompanying drawings, which illustrate a non-limiting embodiment example thereof, wherein.

BEST MODE FOR CARRYING OUT THE INVENTION

Figure 1:
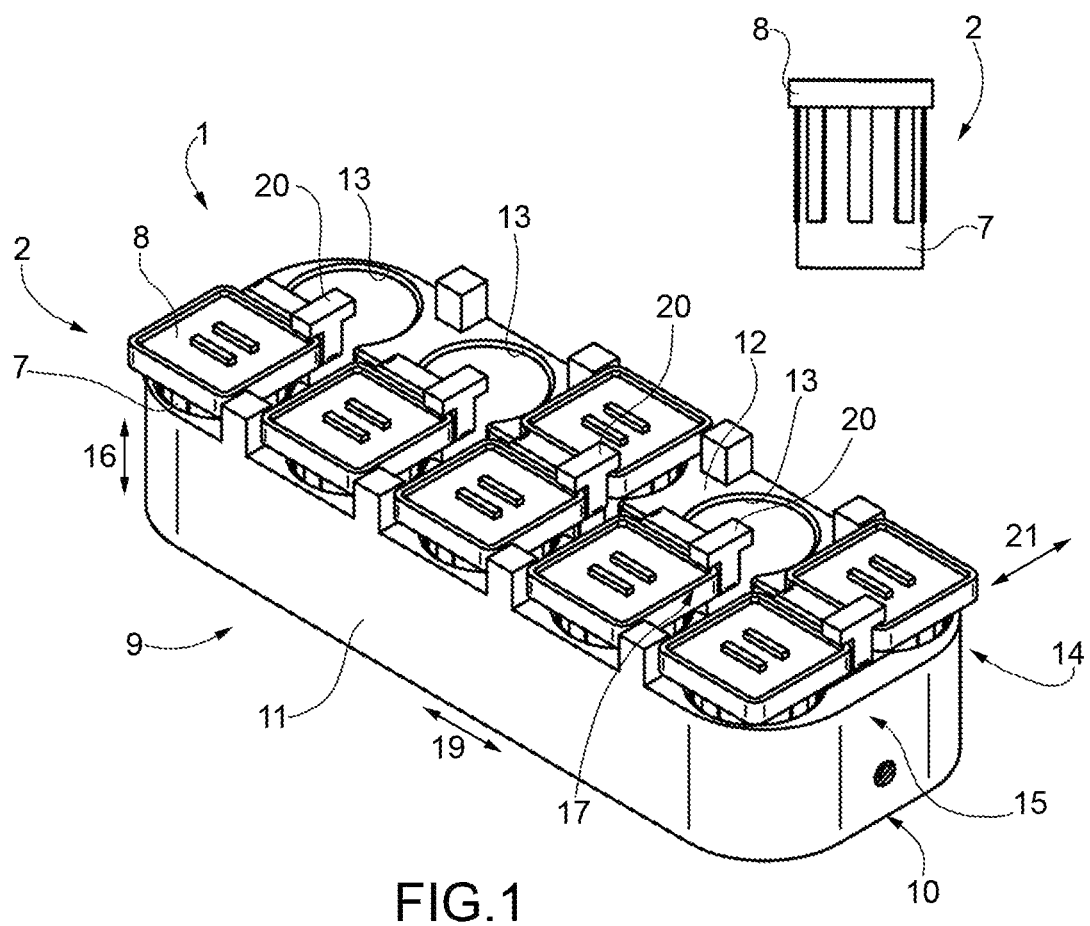
FIG. 1 is a schematic perspective view of a preferred embodiment of the container of the present invention.
Figure 2:
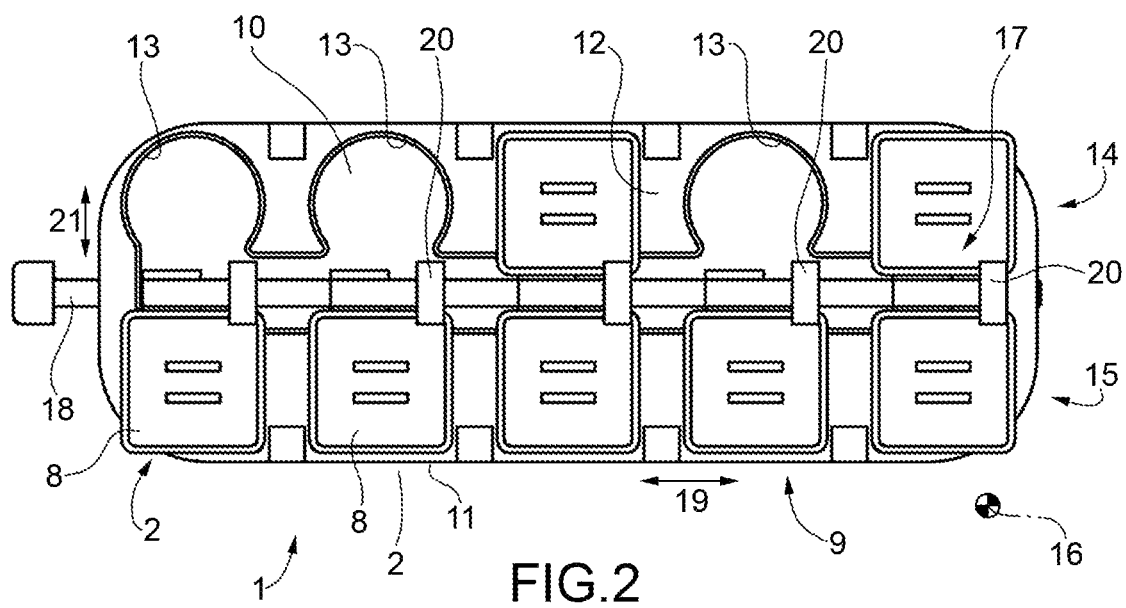
FIG. 2 is a schematic plan view of the container of FIG. 1.

With reference to FIGS. 1 and 2, the number 1 indicates, overall, a container for closing caps 2 for syringes 3 (FIG. 6) each comprising a respective container cylinder 4 provided with an externally threaded open end 5 and a respective piston 6 engaged in a sliding manner in the cylinder 4.

Each cap 2 has a substantially cylindrical lower body 7 and an upper head 8 with substantially quadrilateral shape.

The container 1 comprises a cup-shaped body 9 limited by a substantially flat bottom wall 10 and an annular-shaped lateral wall 11.

The container 1 further comprises a drilled plate 12, which is parallel to the wall 10, extends inside the wall 11, and has a plurality of circular holes defining respective seats 13 for respective caps 2.

The seats 13 are distributed according to two parallel rows 14, 15 of seats 13 which are arranged one next to the other and are configured to be each engaged in a sliding manner by a respective cap 2 in an insertion/extraction direction 16 substantially perpendicular to the wall 10 and to the plate 12.

The caps 2 are retained inside the relevant seats 13 by a locking device 17 comprising a guide rod 18, which is mounted between the two rows 14, 15, and extends in a direction 19 transverse to the direction 16 and parallel to the rows 14, 15.

The rod 18 projects outward from the body 9 in the direction 19, and is coupled in a sliding manner to the body 9 to perform rectilinear movements in said direction 19.

The rod 18 is provided with a plurality of teeth 20, which are equal in number to the number of the seats 13 of a row 14, 15, extend in a direction 21 parallel to the walls 10, 12 and orthogonal to the directions 16, 19, and project from the rod 18 towards the seats 13 of the two rows 14, 15.

The rod 18 is moved, and normally maintained, by a spring (not illustrated) interposed between the body 9 and the rod 18 in a locking position (FIGS. 1 and 2), in which each tooth 20 is arranged above the heads 8 of two adjacent caps 2 of the two rows 14, 15 to lock said caps 2 inside the relevant seats 13.

In other words, when the rod 18 is arranged in its locking position, each tooth 20 defines a closing cover of the relevant seats 13 and locks the relevant caps 2 in the direction 16.

The rod 18 is moved, furthermore, according to procedures which will be better described below, from its locking position to a release position (not illustrated), in which each tooth 20 is arranged between two adjacent pairs of caps 2 to release said caps 2.

Figure 6:
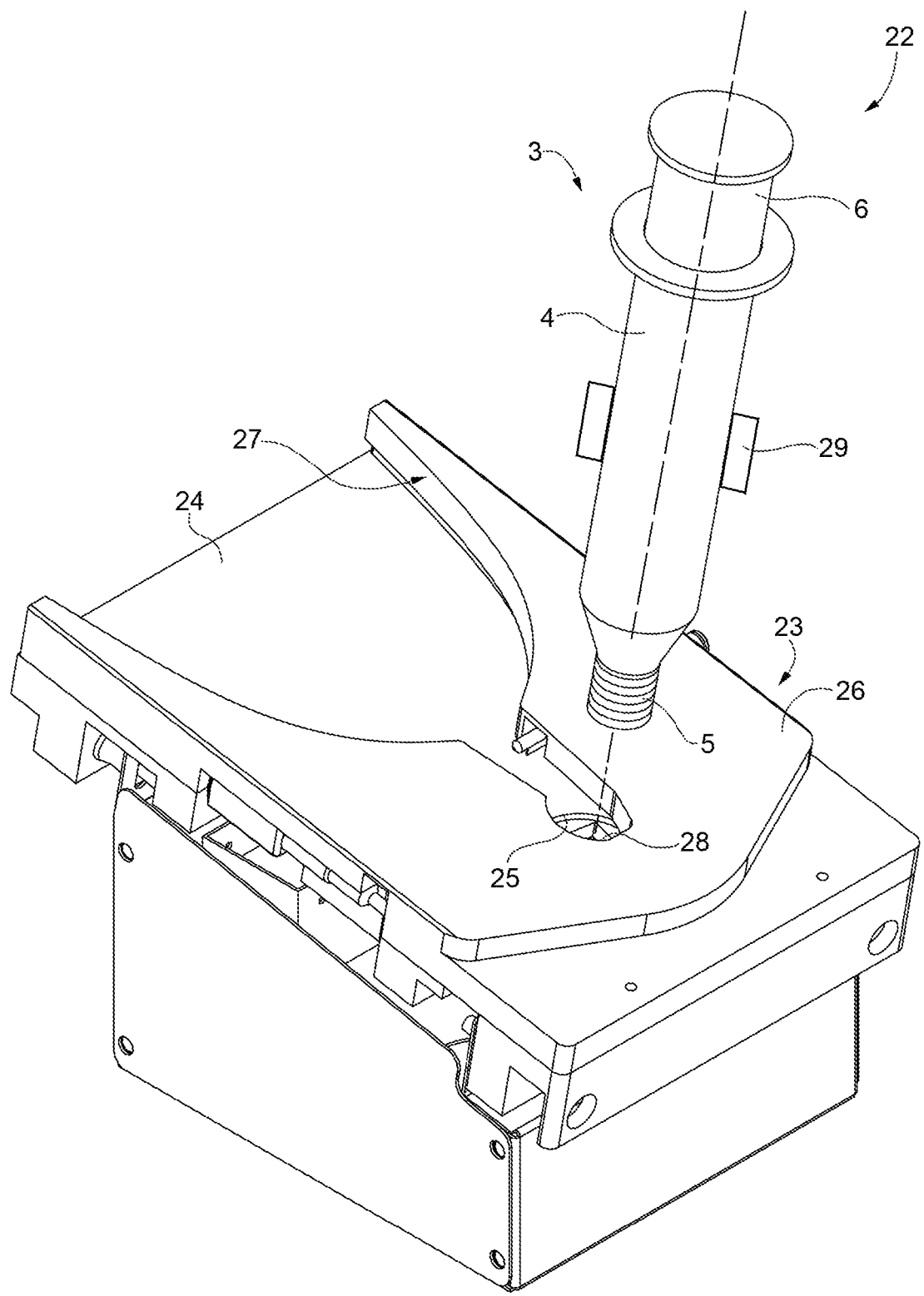
FIG. 6 is a schematic perspective view of a screwdriver assembly for screw-fastening the closing caps.

FIG. 6 illustrates a screwdriver assembly 22 for screw-fastening the caps 2 on the ends 5 of relevant syringes 3.

The screwdriver assembly 22 comprises a container hopper 23 adapted to house inside it a plurality of caps 2 arranged with their concavities facing upwards.

The hopper 23 comprises a vibrating plate 24, which is configured to define a supporting surface P for the caps 2, is inclined by an angle determined with respect to a substantially horizontal reference plane, and has an outlet hole 25 obtained through said plate 24.

The plate 24 is limited laterally by a container plate 26, which has the shape of a fork, and is fixed on the plate 24 to define a feed channel 27, which has a shape converging downwards, and feeds the caps 2 along the surface P and towards the hole 25.

The cap 2 fed forward each time through the hole 25 falls into a pocket 28, which extends below the plate 24, and is mounted on the free end of the output shaft of an electric motor (not illustrated) fitted below said plate 24.

The screwdriver assembly 22 further comprises a robot manipulator 29 configured to maintain the syringe 3 in a position facing the pocket 28.

To screw-fasten each cap 2 on the end 5 of the relevant syringe 3, the pocket 28 with the cap 2 and the robot manipulator 29 with the syringe 3 are moved with respect to each other with a roto-translatory motion.

To load the caps 2 into the hopper 23, the robot manipulator takes a container 1 from a magazine (not illustrated) fitted inside a machine for the preparation of pharmaceutical products, moves the container 1 above the plate 24, and arranges the rod 18 in contact with the plate 26.

So, the rod 18 is moved by the robot manipulator 29 against the plate 26 to its release position so as to allow the caps 2 housed in the container 1 to fall onto the plate 24.

Figure 3:
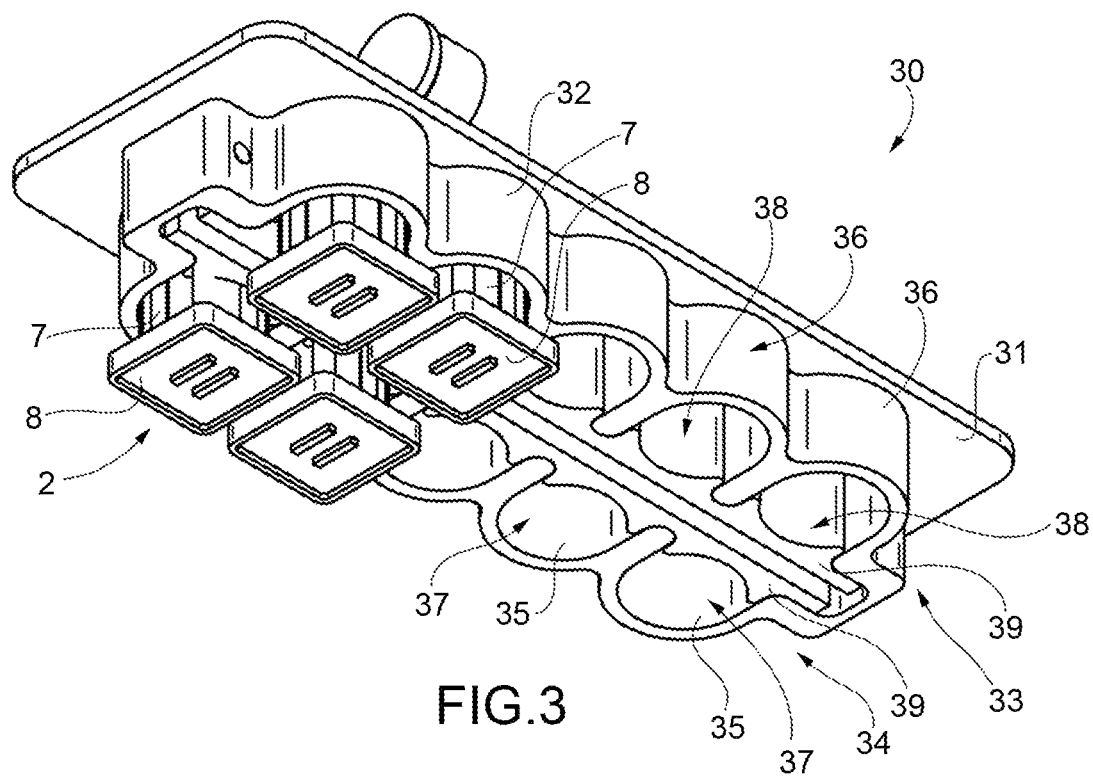
FIGS. 3 and 4 are two schematic perspective views of a variation of the container of FIG. 1.
Figure 4:
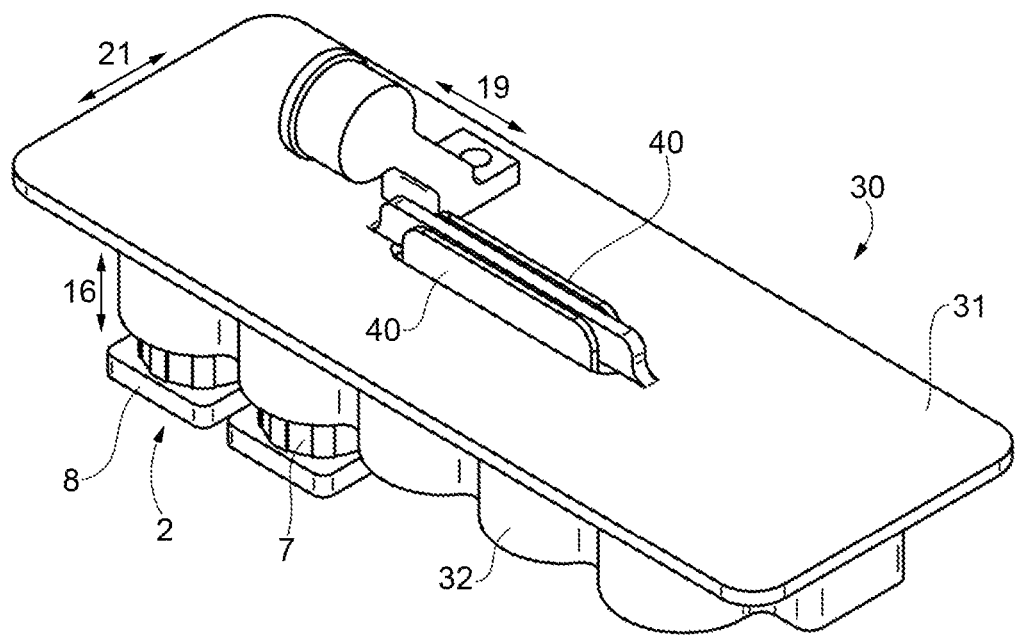
Figure 5:
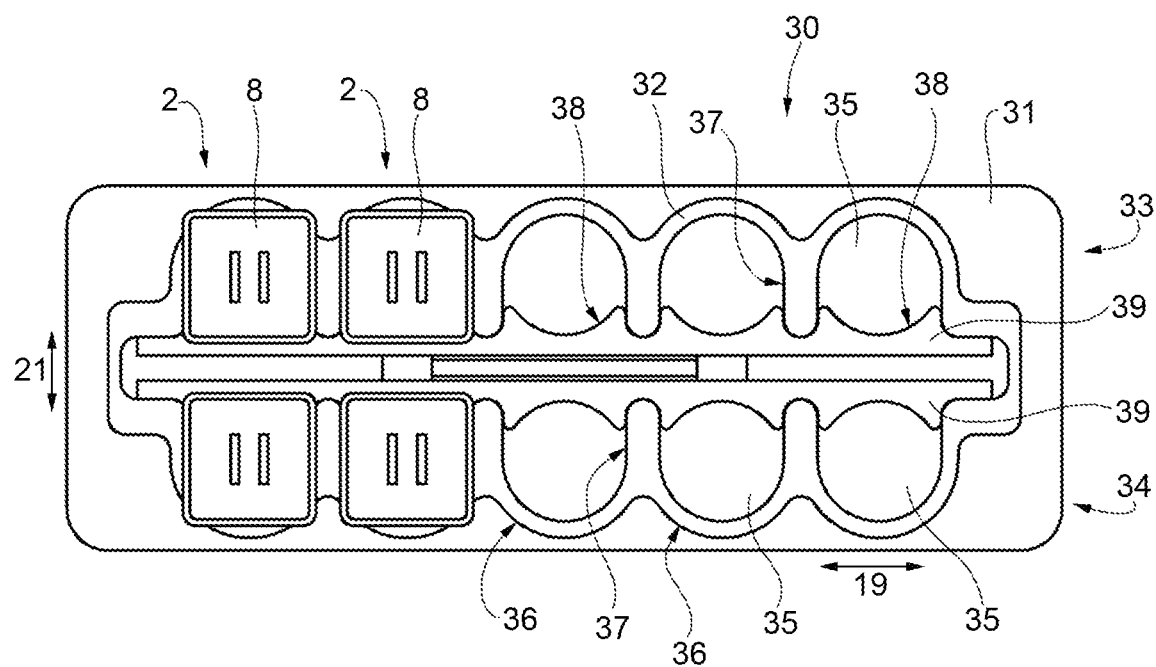
FIG. 5 is a schematic plan view of the container of FIGS. 3 and 4.

The embodiment illustrated in FIGS. 3, 4 and 5 refers to a container 30 comprising a substantially flat bottom wall 31 and an annular-shaped lateral wall 32 projecting from the wall 31.

The container 30 has two rows 33, 34 of seats 35, each of which is configured to be engaged in a sliding manner by a relevant cap 2 in the direction 16.

Each seat 35 of each row 33, 34 is limited by a lateral wall 36 comprising a first portion 37 obtained in the wall 32 and a second portion 38 obtained in a plate 39, which is mounted between the two rows 33, 34 parallel to the direction 19, extends perpendicularly to the wall 31, and is shaped so as to define the portions 38 of all the seats 35 of the relevant row 33, 34.

Each plate 39 has an appendage 40 extending through the wall 31, and is coupled in a sliding manner to the wall 31 to perform rectilinear movements in the direction 21.

Each plate 39 moves between a locking position (FIGS. 3 and 5), in which the plate 39 is moved close to the wall 32 to lock the caps 2 inside the relevant seats 35 in the direction 21, and a release position (not illustrated), in which the plate 39 is moved away from the wall 32 to release the caps 2 onto the plate 24.

In use, the plates 39 are moved from their locking positions to their release positions by the robot manipulator 29, which firstly releases the container 30 onto the plate 24 and then grips the two appendages 40 moving them close to each other.

The configuration of the two containers 1, 30 therefore allows the robot manipulator 29 to collect the container 1, 30 from the magazine (not illustrated) inside the machine for the preparation of pharmaceutical products, discharge the caps 2 onto the vibrating plate 24 of the screwdriver assembly 22, and again discharge the containers 1, 30 into the magazine (not illustrated) fully automatically and without any intervention by the personnel in charge.

The invention claimed is:

1. A container for closing caps (2) for syringes (3), the container comprising a plurality of seats (13; 35), which are suited to be each engaged, in a sliding manner, by a respective closing cap (2); and a guide rod (18), which extends on the outside of the seats (13) and is movable in the alignment direction (19); each tooth projecting from the guide rod (18) transversely to the alignment direction (19);

wherein each of the plurality of seats (13; 35) has a movable portion (20; 38), which is configured to move between a locking position, in which it locks the respective closing cap (2) in one of the plurality of seats (13; 35), and a release position; and wherein the seats (13) are aligned with one another in an alignment direction (19); each movable portion (20) comprising a movable tooth, which moves in the alignment direction (19) between said locking and release positions.

2. Container, according to claim 1, wherein the movable portion (20) is arranged so as to lock the closing cap (2) in the seat (13) parallel to a direction (16) in which the closing cap (2) is inserted/extracted into/from said one of the plurality of seats (13).

3. Container, according to claim 1, wherein the movable portion (20) moves transversely to a direction (16) in which the closing cap (2) is inserted/extracted into/from said one of the plurality of seats (13) between its locking position, wherein the movable portion (20) defines a closing cap of said one of the plurality of seats (13), and its release position, in which the mobile portion (20) is arranged outside of the one of the plurality of seats (13).

4. Container, according to claim 1, wherein, when it is arranged in its release position, each tooth extends between two adjacent seats (13).

5. Container, according to claim 1, wherein the plurality of seats (13) are arranged according to two parallel rows (14, 15) of seats (13), which are arranged one next to the other; the guide rod (18) extending between the two rows (14, 15) of seats (13).

6. Container, according to claim 1, wherein the guide rod (18) projects outwards from the container in the alignment direction (19).

7. Container, according to claim 1, wherein the movable portion (38) is arranged so as to lock the respective closing cap (2) in said one of the plurality of seats (35) transversely to a direction (16) in which the closing cap (2) is inserted/extracted into/from said one of the plurality of seats (35).

8. Container, according to claim 7, wherein each seat (35) is delimited by a lateral wall (36), a part thereof being movable transversely to the insertion/extraction direction (16) so as to define the movable portion (38).

9. Container, according to claim 8, wherein the plurality of seats (35) are aligned with one another in an alignment direction (19); the movable portions (38) of the plurality of seats (35) being obtained in a movable plate (39) extending in the alignment direction (19).

10. Container, according to claim 9, and comprising, furthermore, a bottom wall (31), which is substantially perpendicular to the insertion/extraction direction (16); the movable plate (39) extending through the bottom wall (31), so as to define a hold appendage (40), which projects outwards from the container in order to allow the movable plate (39) to be moved orthogonally to the alignment and insertion/extraction directions (19, 16).

11. Container, according to claim 9, wherein the plurality of seats (35) are arranged according to two parallel rows (33, 34) of seats (35), which are arranged one next to the other; the plurality of seats (35) of each row (33, 34) of seats (35) being delimited by a relevant movable plate (39).

12. A container for closing caps (2) for syringes (3), the container comprising a plurality of seats (13; 35), which are suited to be each engaged, in a sliding manner, by a respective closing cap (2), and a bottom wall (31), which is substantially perpendicular to the insertion/extraction direction (16);

wherein each of the plurality of seats (13; 35) has a movable portion (20; 38), which is configured to move between a locking position, in which it locks the respective closing cap (2) in one of the plurality of seats (13; 35), and a release position;

wherein the movable portion (38) is arranged so as to lock the respective closing cap (2) in the respective seat (35) transversely to a direction (16) in which the closing cap (2) is inserted/extracted into/from said one of the plurality of seats (35);

wherein said one of the plurality of seats (35) is delimited by a lateral wall (36), a part thereof being movable transversely to the insertion/extraction direction (16) so as to define the movable portion (38);

wherein the plurality of seats (35) are aligned with one another in an alignment direction (19); the movable portions (38) of the plurality of seats (35) being obtained in a movable plate (39) extending in the alignment direction (19); and wherein the movable plate (39) extends through the bottom wall (31), so as to define a hold appendage (40), which projects outwards from the container in order to allow the movable plate (39) to be moved orthogonally to the alignment and insertion/extraction directions (19, 16).

\* \* \* \* \*